US006458327B1

(12) United States Patent
Vossmeyer

(10) Patent No.: US 6,458,327 B1
(45) Date of Patent: Oct. 1, 2002

(54) ELECTRONIC DEVICE, ESPECIALLY CHEMICAL SENSOR, COMPRISING A NANOPARTICLE STRUCTURE

(75) Inventor: Tobias Vossmeyer, Fellbach (DE)

(73) Assignee: Sony International (Europe) GmbH, Berlin (DE)

( * ) Notice: Subject to any disclaimer, the term of this patent is extended or adjusted under 35 U.S.C. 154(b) by 0 days.

(21) Appl. No.: 09/487,161

(22) Filed: Jan. 19, 2000

(30) Foreign Application Priority Data

Jan. 21, 1999 (EP) ............................................ 99101141

(51) Int. Cl.⁷ .............................................. G01N 15/06
(52) U.S. Cl. ...................... 422/68.1; 422/82.01; 422/98
(58) Field of Search ............................. 422/68.1, 82.01, 422/98; 436/171

(56) References Cited

U.S. PATENT DOCUMENTS 5,589,537 A     12/1996  Golden et al.
6,057,556 A  *  5/2000   Gubin et al. ................... 257/39
6,242,264 B1 *  6/2001   Natan et al. ................. 436/171

FOREIGN PATENT DOCUMENTS

EP          0 865 078        9/1998
WO          WO 96 07487      3/1996

OTHER PUBLICATIONS

Wohltjen H. et al.: "Colloidal Metal—Insulator–Metal Ensemble Chemiresistor Sensor" Analytical Chemistry, vol. 70, No. 14, Jul. 15, 1998, pp. 2856–2859, XP000778883.
Nayral C et al.: "A Novel Mechanism for the Synthesis of Tin/Tin Oxide Nanoparticles of Low Size Dispersion and of Nanostructured SNO2 for the Sensitive Layers of Gas Sensors", Advanced Materials, DE, VCH Verlagsgesellschaft, Weinheim, vol. 11, No. 1, pp. 61–63 XP000790794 ISSN: 0935–9648.

* cited by examiner

Primary Examiner—Lyle A. Alexander
Assistant Examiner—Samuel P Siefke
(74) Attorney, Agent, or Firm—Frommer Lawrence Haug LLP; William S. Frommer; Samuel H. Megerditchian

(57) ABSTRACT

Disclosed is an electronic device comprising a nanoparticle structure and configured such that, when driven by a power source, a current path is defined through said nanoparticle structure, wherein the nanoparticle structure comprises a substrate and metal and/or semiconductor nanoparticles, wherein the nanoparticles are linked to each other and/or to the substrate by bifunctional or polyfunctional ligands. The invention especially relates to an electronic device in the form of a sensor for detecting one or more analytes in a liquid or a gas phase.

21 Claims, 2 Drawing Sheets

Figure 1:
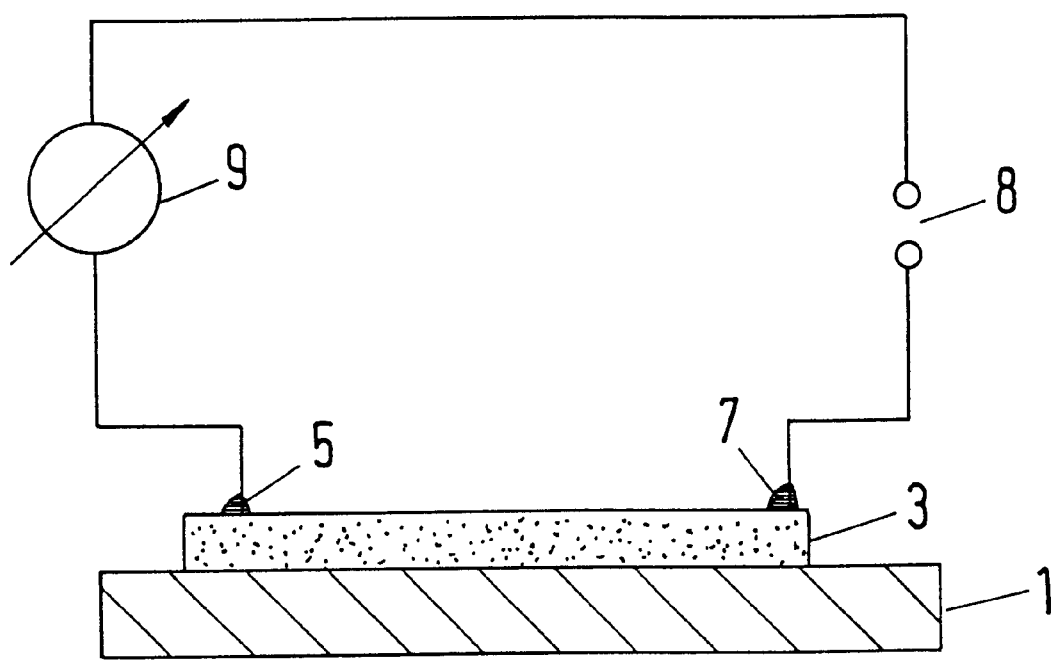

ELECTRONIC DEVICE, ESPECIALLY CHEMICAL SENSOR, COMPRISING A NANOPARTICLE STRUCTURE

This invention relates to an electronic device according to the first part of claim 1 and especially to the use of such electronic devices as sensors for detecting analytes in the fluid or gas phase.

Chemical sensors for inorganic gases gain an increasing importance in connection with the control of chemical processes and environmental issues. A wide variety of chemical sensors for inorganic gases and organic gases is available on the market. A problem with most chemical sensors is that they are not able to detect small concentrations of analytes, e.g. in the range of 10 ppm and below. Semiconductor sensors are known which are more sensitive and which can operate in a range of about 0.1 to 1 ppm. These sensors rely on the effect that the semi-conductor changes its conductivity after adsorption of analyte molecules. However, such semiconductor sensors are usually rather unstable and therefore unreliable. Furthermore, the interaction between the semiconductor layer and the analyte usually has to be of the donor-acceptor type to gain a measurable change of conductivity.

Recently, H. Wohltjen and A. W. Snow, Anal. Chem. 1998, 70, 2856 proposed a new type of sensor, comprising gold nanoparticles deposited on a quartz substrate comprising a micro-electrode structure. The nanoparticles were deposited on the substrate by spraying (airbrush technique). The conductivity of the nanoparticle layer changed with the concentration of toluene vapour in the surrounding atmosphere and allowed a detection of toluene down to 2.7 ppm. Experiments with tetrachloroethylen (TCE) and propanol showed a significant dependence of the conductivity on the concentration of the analyte for TCE and a weak dependence for propanol.

Although the sensor described in this paper has many desirable features, it may however not be suitable for detection in the liquid phase due to its structure. Furthermore, there is only limited control over the electronic and chemical properties of the device.

It is the object of the present invention to provide an electronic device comprising a nanoparticle structure, which is especially suitable for use as a sensor and which can be more closely tailored to the needs of an analytic process.

This object is accomplished by an electronic device which comprises a nanoparticle structure and is configured such that a current can be conducted through said nanoparticle structure, and which is characterized in that the nanoparticle structure comprises a substrate and semi-conductor and/or metal nanoparticles, wherein the nanoparticles are linked to each other and/or to the substrate by bifunctional or polyfunctional ligands.

The substrate may especially consist of glass or of a semiconductor. The latter is preferred if the device is used in an integrated structure. The nanoparticles preferably are made of good conductors. In order to provide chemical stability it is preferred that the material is chemically inert as well so that gold or platinum are especially preferred. The function of the bifunctional or polyfunctional ligands is to connect two or more nanoparticles so that a structure is formed that is both mechanically and electrochemically stabilized.

In a preferred embodiment of the invention the nanoparticles are arranged in layers, wherein nanoparticles in each of said layers and nanoparticles of adjacent layers are interconnected by one or more of said ligands.

Preferably, the ligands interconnecting the nanoparticles are basically of the same length, although it may also be envisaged to use ligands of different lengths, for example connecting layers and for connecting nanoparticles within one layer, respectively.

In a preferred embodiment it is provided that said ligands comprise one or more amino groups and/or one or more thiol groups.

The ligands may be chosen from the group comprising mercaptoalkylsilanes, aminoalkylsilanes, dimercaptoalkanes, diaminoalkanes and hydroxy- and carboxy-alkanes, especially dihydroxyalkanes and dicarboxyalkanes. Not only alkanes, but also bi- and polyfunctional organic and/or inorganic compounds may be used as linkers (ligands).

According to a specific embodiment, the nanoparticle structure is integrated together with a transistor structure to form a controlling element for current between terminals of the transistor.

The invention also provides an electronic device, especially as set out above, wherein a (resonant) tunneling structure is formed by one or more layers of nanoparticles sandwiched between insulating barriers and this tunneling structure is arranged to control a transistor by the current flowing therethrough in response to a voltage applied to the (resonant) tunneling structure.

The invention is especially directed to the use of a device as set out above as a sensor for detecting one or more analytes in a liquid or gas phase, wherein the analyte is detected by a change of conductivity of the nanoparticle structure.

Furthermore, the invention provides a sensor for detecting one or more analytes in a liquid or gas phase, especially a sensor forming an electronic device as set out previously, comprising a nanoparticle structure, which is accessible to an analyte in the environment of the sensor, and means for detecting the conductivity of said nanoparticle layer, characterized in that the nanoparticle structure comprises a substrate and semiconductor and/or metal nanoparticles, wherein the nanoparticles are linked with each other and/or the substrate by bifunctional or polyfunctional ligands.

Preferably the means for detecting the conductivity of said nanoparticle layer work according to an electric measurement principle, i.e. they detect the current flowing for a given voltage. Standard resistance/conductivity measuring circuits may be used. Although this is the preferred embodiment, other ways for detecting the conductivity of the nanoparticle layer and related means could be contemplated for use in the sensor according to the invention, especially means for optically determining the conductivity, e.g. by optically measuring the complex dielectric function of the nanoparticle structure.

The invention may especially provide that the ligands define cavities having a size greater or equal to that of the analyte to be detected.

It can be furthermore be provided that the ligands comprise chains and/or side chains to promote the adsorption of a specific analyte and/or to prevent or hinder the adsorption of substances other than said analyte.

Furthermore, the invention may provide that the surface of at least of some nanoparticles is modified to favour adsorption of a specific analyte and/or hinder or prevent adsorption of substances other than said analyte.

The invention especially applies to a sensor that it is adapted to detect one ore more of the following substances: ammonia, ethanol, propanol, water, aliphatic and aromatic hydrocarbons.

According to a specific embodiment of the invention it may be provided that the sensor comprises an amplifying element controlled by the current flowing through the nanoparticle structure.

Especially, the nanoparticle structure may be arranged such that it controls the base current of a bipolar transistor through changes of its conductivity.

Furthermore, it can be provided that the nanoparticle structure is enclosed between two tunneling barriers and forms a resonant tunneling device controlling the amplifying element.

Preferably the nanoparticle structure is integrated together with said amplifying element in an integrated circuit (IC).

According to a specific embodiment, a chemically selective membrane is provided on top of the nanoparticle structure so that it is exposed to the analyte, or within the nanoparticle structure.

The invention also provides an advantageous method to produce a nanoparticle structure for use in devices in sensors as described above, which are characterized in that self-assembly techniques are employed. Especially, such a method may comprise the following steps:

a) linking a first layer of nanoparticles to a substrate by ligand molecules,
b) linking bifunctional or polyfunctional ligands to said first layer of nanoparticles,
c) linking a further layer of nanoparticles to said bifunctional or polyfunctional ligands, wherein steps b) and c) may be repeated to create a plurality of stacked nanoparticle monolayers on said substrate. Preferably, the nanoparticle layers are essentially monolayers.

Preferably the entire nanoparticle structure has a thickness in the range of 50 to 100 nm. In the preferred embodiments, the nanoparticle structure comprises about 10 to 20 layers.

The term "nanoparticle", as used in the context of this application, is to be understood as a particle having a relevant length scale of 1 $\mu$m or less. It is preferred to use structures with particles having a diameter of 100 nm or less, more preferably 20 nm or less.

It has turned that the above-mentioned electronic device and sensors according to the present invention are very well suited as sensors for detecting the analyte and measuring the analyte concentration through a change of conductivity. They show a significant change (increase or decrease) of conductivity upon absorption of an analyte, such as ammonia, ethanol, propanol, hexanes, water or toluene. Due to their structure and especially the cross-linking bifunctional or polyfunctional ligands, they are more stable and especially suitable for detection in the liquid phase. They have a high surface to volume ratio and afford low signal to noise ratios.

By using bifunctional or polyfunctional ligands it is also possible to define the location of the nanoparticles with regard to each other and to the substrate in a much more precise manner as according to the prior art. Especially, by adjusting the size of the ligands and thus the size of the cavities between the nanoparticles, the size of these cavities can be adjusted to fit the size of an analyte molecule, which can therefore diffuse in and out of these cavities, thereby changing the conductivity of the structure. According to advantageous embodiments, it is possible to promote the selectivity by providing the ligands and/or the surface of the nanoparticles with desirable chemical properties favouring the adsorption of the analyte and preventing or hindering the adsorption of undesired substances. The new nanoparticle structure according to the invention is not only useful for sensors, but also for producing other electronic devices where well defined properties, especially a well defined conductance, are desirable or necessary. Especially, such electronic devices may comprise a resonant tunneling transistor, wherein the tunneling element is formed by at least one nanoparticle structure between two insulating barriers. Resonant tunneling transistors are described, for example, in Michael S. Montemerlo et al., Technologies and Designs for Electronic Nanocomputers, The MITRE Corporation, McLean, Va., 1996, p. 10 et seq. With regard to details of the structure of a resonant tunneling transistor, explicit reference is made to this document and the related publications cited therein, especially J. M. Rabaey, Digital Integrated Circuits: A Design Perspective, Prentice Hall, 1996 and A. C. Seabaugh et al, IEEE Transactions on Electronic Devices, Vol. 36, No. 10, 1989, pp. 2328–2334 and Appl. Phys. Lett., Vol. 59, 1991, pp. 3413–3415. The invention proposes to replace the resonant tunneling device which was provided in the above-mentioned prior art together with a transistor to result in a resonant-tunneling transistor and which was made by conventional techniques, e.g. employing semiconductors, by a resonant tunneling device comprising a nanoparticle structure having tunneling barriers on both sides. Especially referring to such resonant tunneling transistors, it should be understood that the present application is not limited to transistors having a nanoparticle structure comprising bifunctional or polyfunctional ligands and rather comprises also embodiments wherein the nanoparticle structure is of a different nature.

Further features and advantages of the present invention will be apparent from the detailed description of a specific embodiment in connection with the drawings.

Figure 2:
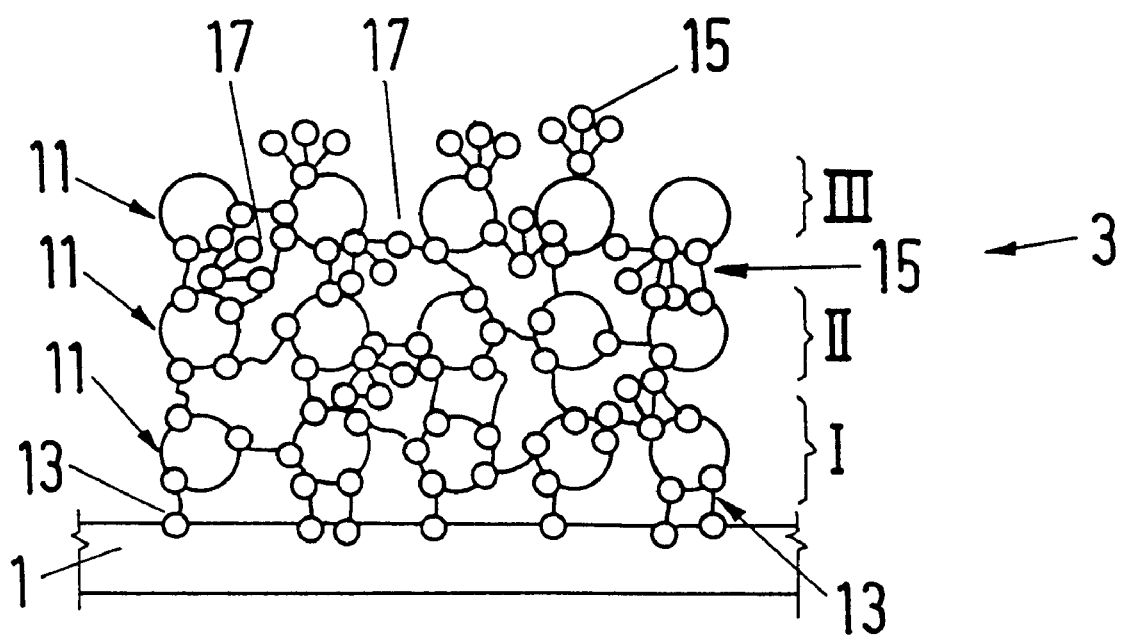

FIG. 1 schematically shows a simplified diagram of a circuit comprising an electronic device according to the present invention for use as a chemical sensor and FIG. 2 schematically shows the nature of the nanoparticle structure employed according to the present invention.

In the embodiment schematically shown in FIG. 1, the electrochemical sensor according to the present invention comprises a substrate 1, which may be a glass plate, a silicon wafer or the like, carrying a nanoparticle structure 3. On the nanoparticle structure there are contacts 5, 7 to be connected with a power supply 8 and a current measuring device 9 for determining the conductivity or resistance of the nanoparticle structure. The contacts 5 and 7 may be of any suitable form and may especially be finger electrodes or interdigitated electrodes. The precise location of these contacts is only relevant in that they should allow measuring the conductivity of the nanoparticle structure in a reliable way. For example, it could be envisaged to provide them on the substrate.

FIG. 2 shows the nanoparticle structure and its connection to the substrate schematically in more detail. On the substrate 1 a first layer I of nanoparticles 11 is provided, which are linked to the substrate by linking molecules or ligands 13. Suitable ligands for fixing the nanoparticles to a substrate are well known and available to people skilled in the art. For example, if the nanoparticles consist of gold and a glass substrate is used, a suitable ligand is 3-aminopropyltriethoxysilane. The nanoparticles 11 of layer I are also linked with each other through ligands 15, which are preferably different from the ligands 13 linking the nanoparticles to the substrate. Such ligands may especially be mercaptoalkylsilanes, aminoalkylsilanes, dimercaptoalkanes, diaminoalkanes or polyfunctionalized polymers.

Overlying the first layer of nanoparticles there is a second layer II of nanoparticles 11 which are linked to the nanoparticles of the first layer I by said ligands 15 and also linked with each other within the layer through ligands 15, as previously described with regard to layer I. On the second layer, there may be one or more further layers (III) of nanoparticles which are interlinked within the layer and to the layer below in the manner previously described. Preferably, in order to allow an easy diffusion of analytes, the nanoparticle layer should be thin, but thick enough to allow a conductivity in a range that can be readily detected. A presently preferred range for the thickness of the nanoparticle structure is about 50 to 100 nm.

In order to improve the selectivity of the sensor, a selective membrane may be arranged on top of the uppermost nanoparticle layer or embedded in the nanoparticle structure. Such membranes may be manufactured in a variety of manners, especially by molecular imprinting techniques (cf. S. W. Lee et al, Langmuir, 1998, 14, 2857; F. L. Dickert et al, Adv. Mater. 1998, 10, 149), which also allow to implement a selective membrane or structure within the nanoparticle structure.

From FIG. 2 it can be seen that the ligands connecting nanoparticles 11 define cavities into which analyte molecules 17 may diffuse. If analyte molecules occupy these cavities, the conductivity of the nanoparticle structure changes. It was shown that the amount and direction of the change (positive or negative) may be specific for different analytes. Depending on the nature of the analyte and the materials used to build the nanoparticle structure, adsorption to the nanoparticles and/or to the ligands may also take place. By tailoring the size of these cavities to the size of the analyte molecules to be detected, which can be done by choosing an appropriate length of the hydrocarbon chain of the ligands, selectivity can be achieved in a controlled manner. Furthermore, adsorption of analyte molecules may be promoted by adjusting the chemical properties of the nanoparticles and/or the ligands in a manner well known per se. For example, hydrophilic, hydrophobic, aromatic or otherwise chemically functionalized chains and side chains may be introduced to the ligands so that an adsorption of the analyte is promoted and the adsorption of undesired substances, e.g. water, is prevented.

Likewise, the nanoparticles may be chosen to consist of a suitable metal and/or to have a surface treated for promoting the adsorption of a specific analyte. Generally, good conductors, such as gold or platinum, which are also chemically inert, are preferred as basic materials for the nanoparticles in order to get a good conductivity signal. However, other materials showing an acceptable conductivity and chemical stability, especially semiconductors, are also contemplated.

Preferred methods to provide a layered structure as shown in FIG. 2 are self-assembly methods which are well known in the art per se. Basically, self-assembly methods provide to prepare a substrate surface with linking molecules linking to the substrate and able to link to the envisaged nanoparticles as well. On the substrate surface thus prepared a first layer of nanoparticles is provided which are linked to said linking molecules. In the next step multifunctional ligands linking to the nanoparticles are added to which a new layer of nanoparticles is linked in the next step and so on so that by adding step by step nanoparticles and multifunctional ligands a layered structure is formed.

EXAMPLE

In order to prepare a sensor according to the present invention, nanoparticles were prepared as described in D. V. Leff, L. Brandt, J. R. Heath, Langmuir, 1996, 12, 4723, using dodecylamine as a stabilizing ligand. The particles were deposited and chemically linked onto a glass substrate by the use of 3-aminopropyltriethoxysilane. The particles were chemically linked with each other and self-assembled by the use of 1,6-dimercaptohexane. The nanoparticle structure thus created consists of several layers of self-assembled nanoparticles. Contacts were applied and connected to a resistance measuring circuit. The sensors thus built showed a response of the conductivity to ammonia in the sub-second response time regime with a good signal-to-noise ratio. The response was reversible and thus the suitability of this structure for sensor purposes was demonstrated.

Similar experiments were carried out for ethanol, propanol, water, hexanes, toluene and other analytes. The changes in conductivity were up to 30% and mostly occurred in the sub-second response time regime when the film was exposed to the analyte vapour.

It was also shown that the selectivity and the sensitivity of the device towards the analytes could be adjusted by heating the structure before using as a sensor. For example, the response to an exposure to ammonia or water changed from an increase to a decrease of conductivity after curing it at elevated temperature. The use of a long-chain dithiolalkanes as bifunctional linkers between the nanoparticles improved the sensitivities towards some organic compounds.

Due to the use of nanoparticles, the sensor according to the invention has a high sensitivity with a high signal-to-noise ration even for low analyte concentrations. Due to the linking of the nanoparticles, the structure is more stable than according to the prior art. Especially, stability against humidity can be achieved again by introducing hydrophobic linkers between the particles.

The features of the present invention disclosed in the specification, the claims and/or in the accompanying drawings may, both separately and in any combination thereof, be material for realizing the invention in various forms thereof.

What is claimed is:

1. A nanoparticle structure for use in an electronic device configured such that a current can be conducted through said nanoparticle structure, comprising:
  a) a substrate;
  b) nanoparticles connected to the substrate and to each other by one or more bifunctional or polyfunctional ligands; and
  c) cavities for diffusion of an analyte therein and formed from the voids created by the connection of the nanoparticles to each other, wherein the nanoparticles are selected from the group consisting of a metal and a semiconductor; wherein the ligands connecting the nanoparticles to each other are different from the ligands connecting the nanoparticles to the substrate; and wherein said nanoparticle structure is adapted to be integrated in an integrated circuit with an amplifying element controlled by the current flowing through the nanoparticle structure.

2. The nanoparticle structure according to claim 1, wherein the nanoparticles are arranged in layers, and wherein the nanoparticles in each of said layers and the nanoparticles of adjacent layers are connected by one or more of said ligands.

3. The nanoparticle structure according to claim 1, wherein said ligands comprise one or more amino groups.

4. The nanoparticle structure according to claim 1, wherein said ligands comprise one or more thiol groups.

5. The nanoparticle structure according to claim 1, wherein the ligands are selected from the group consisting of mercaptoalkylsilanes, aminoalkylsilanes, dimercaptoalkanes, dithiolalkanes, diaminoalkanes, dihydroxyalkanes and dicarboxyalkanes.

6. The nanoparticle structure according to claim 1, wherein the nanoparticle structure is integrated with a transistor structure comprising terminals so as to form a controlling element for current between the terminals of the transistor.

7. The nanoparticle structure according to claim 6, wherein a resonant tunneling structure is formed by one or more layers of nanoparticles sandwiched between insulating barriers, wherein the tunneling structure is arranged to control the transistor by the current flowing therethrough in response to a voltage applied to the resonant tunneling structure.

8. A sensor having a nanoparticle structure for detecting one or more analytes in a liquid or gas phase and configured such that a current can be conducted through said nanoparticle structure, the nanoparticle structure comprising:
   a) a substrate;
   b) nanoparticles connected to the substrate and to each other by one or more bifunctional or polyfunctional ligands;
   c) cavities for diffusion of an analyte therein and formed from the voids created by the connection of the nanoparticles to each other;
   d) means for detecting the conductivity of said nanoparticles; and
   e) an amplifying element controlled by the current flowing through the nanoparticle structure, wherein the nanoparticles are selected from the group consisting of a metal and a semiconductor; and wherein the ligands connecting the nanoparticles to each other are different from the ligands connecting the nanoparticles to the substrate.

9. The sensor according to claim 8, wherein the cavities have a size greater or equal to that of the analyte to be detected.

10. The sensor according to claim 8, wherein the ligands comprise chains and/or side chains to promote the adsorption of a specific analyte and/or to prevent or hinder the adsorption of substances other than said analyte.

11. The sensor according to claim 8, wherein at least some nanoparticles favor the adsorption of a specific analyte and/or hinder or prevent adsorption of substances other than said analyte.

12. The sensor according to claim 8, wherein the analyte is selected from the group consisting of ammonia, ethanol, propanol, toluene, water, and hexanes.

13. The sensor according to claim 8, wherein the nanoparticle structure is arranged such that it controls the base current of a bipolar transistor through changes of its conductivity.

14. The sensor according to claim 8, wherein the nanoparticle structure is enclosed between two tunneling barriers thereby forming a resonant tunneling device.

15. The sensor according to claim 8, wherein the nanoparticle structure is integrated together with said amplifying element in an integrated circuit.

16. The sensor according to claim 8, further comprising a chemically selective membrane positioned on top of or within the nanoparticle structure.

17. A method for producing a nanoparticle structure for use in an electrical device which comprises said nanoparticle structure and is configured such that a current can be conducted through said nanoparticle structure, the nanoparticle structure comprising a substrate and metal and/or semiconductor nanoparticles, wherein the nanoparticles are linked to each other and/or to the substrate by bifunctional or polyfunctional ligands, wherein the ligands connecting the nanoparticles to each other are different from the ligands connecting the nanoparticles to the substrate, and wherein said nanoparticle structure is adapted to be integrated in an integrated circuit with an amplifying element controlled by the current flowing through the nanoparticle structure, said method comprising the steps of:
   a) linking a first layer of nanoparticles to a substrate by ligand molecules;
   b) linking bifunctional or polyfunctional ligands to said first layer of nanoparticles, and
   c) linking a further layer of nanoparticles to said bifunctional or polyfunctional ligands.

18. The method according to claim 17, wherein steps b) and c) are repeated to create a plurality of stacked nanoparticle monolayers on said substrate.

19. A sensor for detecting one or more analytes in a liquid or gas phase, comprising:
   a) a nanoparticle structure comprising a substrate and metal and/or semiconductor nanoparticles, wherein the nanoparticles are linked to each other and/or to the substrate by bifunctional or polyfunctional ligands;
   b) means for detecting the conductivity of said nanoparticle structure; and
   c) an amplifying element controlled by a current flowing through the nanoparticle structure.

20. The sensor according to claim 19, wherein the nanoparticle structure is enclosed between two tunneling barriers thereby forming a resonant tunneling device.

21. The sensor according to claim 20, wherein the nanoparticle structure is integrated together with said amplifying element in an integrated circuit.

* * * * *